(12) United States Patent
Foster

(10) Patent No.: US 6,178,652 B1
(45) Date of Patent: Jan. 30, 2001

(54) MEASURING APPARATUS

(76) Inventor: Andrew John Foster, 22 Station Street, Walsall, West Midlands WS2 9JZ (GB)

(*) Notice: Under 35 U.S.C. 154(b), the term of this patent shall be extended for 0 days.

(21) Appl. No.: 09/063,953

(22) Filed: Apr. 21, 1998

(30) Foreign Application Priority Data

Apr. 24, 1997 (GB) .................................................. 9708306

(51) Int. Cl.$^7$ .............................. G01B 1/00; G01B 5/02
(52) U.S. Cl. ................................. 33/511; 33/759; 54/6.1
(58) Field of Search .................... 33/511, 512, 555.1, 33/555.4, 755, 759, 760, 770, 768, 484, 486, 488; 54/6.1, 6.2, 7, 8, 16, 17

(56) References Cited

U.S. PATENT DOCUMENTS

| | | | |
|---|---|---|---|
| 325,134 | * | 8/1885 | Wainwright ............................ 33/511 |
| 402,068 | * | 4/1889 | Crannell ................................. 33/511 |
| 650,136 | * | 5/1900 | Runnette ................................ 33/770 |
| 846,661 | * | 3/1907 | Engel ..................................... 33/755 |
| 3,604,183 | * | 9/1971 | Iseli ........................................ 54/6.1 |
| 4,635,367 | * | 1/1987 | Vigede ................................... 33/512 |
| 4,722,171 | * | 2/1988 | Meroth ................................... 54/6.1 |
| 4,843,720 | * | 7/1989 | Kim ....................................... 33/512 |
| 4,875,296 | | 10/1989 | Holzmeister et al. . |
| 4,920,659 | | 5/1990 | Becher . |
| 4,953,345 | * | 9/1990 | Boone .................................... 54/6.1 |
| 5,174,030 | | 12/1992 | Clot et al. . |
| 5,697,163 | * | 12/1997 | Ulrich .................................... 33/511 |
| 5,732,475 | * | 3/1998 | Sacks ..................................... 33/555 |

FOREIGN PATENT DOCUMENTS

0865986 * 2/1953 (DE) ..................................... 33/759

* cited by examiner

Primary Examiner—Diego Gutierrez
Assistant Examiner—F. Francis
(74) Attorney, Agent, or Firm—Smith-Hill and Bedell

(57) ABSTRACT

Apparatus 10 for measuring the head of a horse 12 incorporates various components, such as cheek straps 14, each of which is movable (slidable) relative to another component in order to produce an overall desired fit of the apparatus 10, which is generally in the form of a bridle, to the head 12. Once the desired fit has been achieved, windows 16 and numerals 18 allow measurements to be taken, indicating the relative positions of the slidable components. These measurements may give direct measurements of the lengths required of various components of the bridle to be made, or may be other measurements from which strap lengths can be deduced. The apparatus 10 generally resembles the bridle which will be constructed, and thus allows the user to ensure a good fit to a particular head (which is partly an aesthetic judgement, and partly based on measurement and experience), so that a bridle can then be made with reasonable confidence that it will be a good fit.

8 Claims, 4 Drawing Sheets

MEASURING APPARATUS

The present invention relates to measuring apparatus and particularly, but not exclusively, to apparatus for measuring the head of a horse in order to produce a well fitting bridle.

A bridle is an important part of the means by which a rider controls a horse. An ill fitting bridle can reduce the effectiveness of the rider's control, with consequent safety implications, and can be uncomfortable for the horse, which can cause injury to the horse or cause the horse to be less cooperative, again with safety implications.

According to the invention, there is provided horse head measuring apparatus comprising two components which are movable relative to one another to produce a desired fit of the apparatus relative to the head, and measuring means operable to provide a measurement of the relative positions of the components.

Preferably the measuring means comprise indicia associated with one of the components, and indicator means associated with the other component, the indicator means serving, in use, to indicate one of the indicia as the aforesaid measurement. The indicator means may comprise a window through which the indicated one of the indicia is visible. The said one of the components may be elongate, and carry the indicia along its length, the window being formed on the other of the components, and the said one component being slidable relative to the other component to present indicia through the window according to the relative positions. The said other component preferably comprises two apertures, the one component being threaded through both apertures in opposite senses to be visible between the apertures and to be obscured by the other component to either side of the apertures.

Preferably the indicia are numerical. The indicia may represent the length required of a strap of a finished harness article having the desired fit to the head being measured. Preferably the finished harness article is a bridle.

The apparatus preferably forms a bridle, there being measuring means as aforesaid at each position at which an adjustable connection will be provided for a strap in the bridle to be made from the measurements, whereby the length required of each strap in the bridle is represented by respective indicia after the apparatus has been adjusted to provide the desired fit to the head.

The invention also provides a method of measuring a horse's head, in which components which are movable relative to each other are offered to the head and adjusted relative to one other to achieve a desired fit to the head, and in which measuring means are used to provide a measure of the relative positions of the components.

Preferably the components form part of the measuring apparatus as aforesaid, and wherein the or each of the relatively movable components are moved until a desired overall fit is achieved by the apparatus, and measurements are then read from the or each measurement means.

A measuring apparatus may be dispatched to a prospective customer by a manufacturer, the customer fitting the apparatus to the head, recording the measurements provided by the measurement means, and providing the measurements to the manufacturer, whereby the manufacturer may produce a made-to-measure harness article without access to the horse.

One example of apparatus according to the present invention will now be described in more detail, by way of example only, and with reference to the accompanying drawings, in which.

Figure 1:
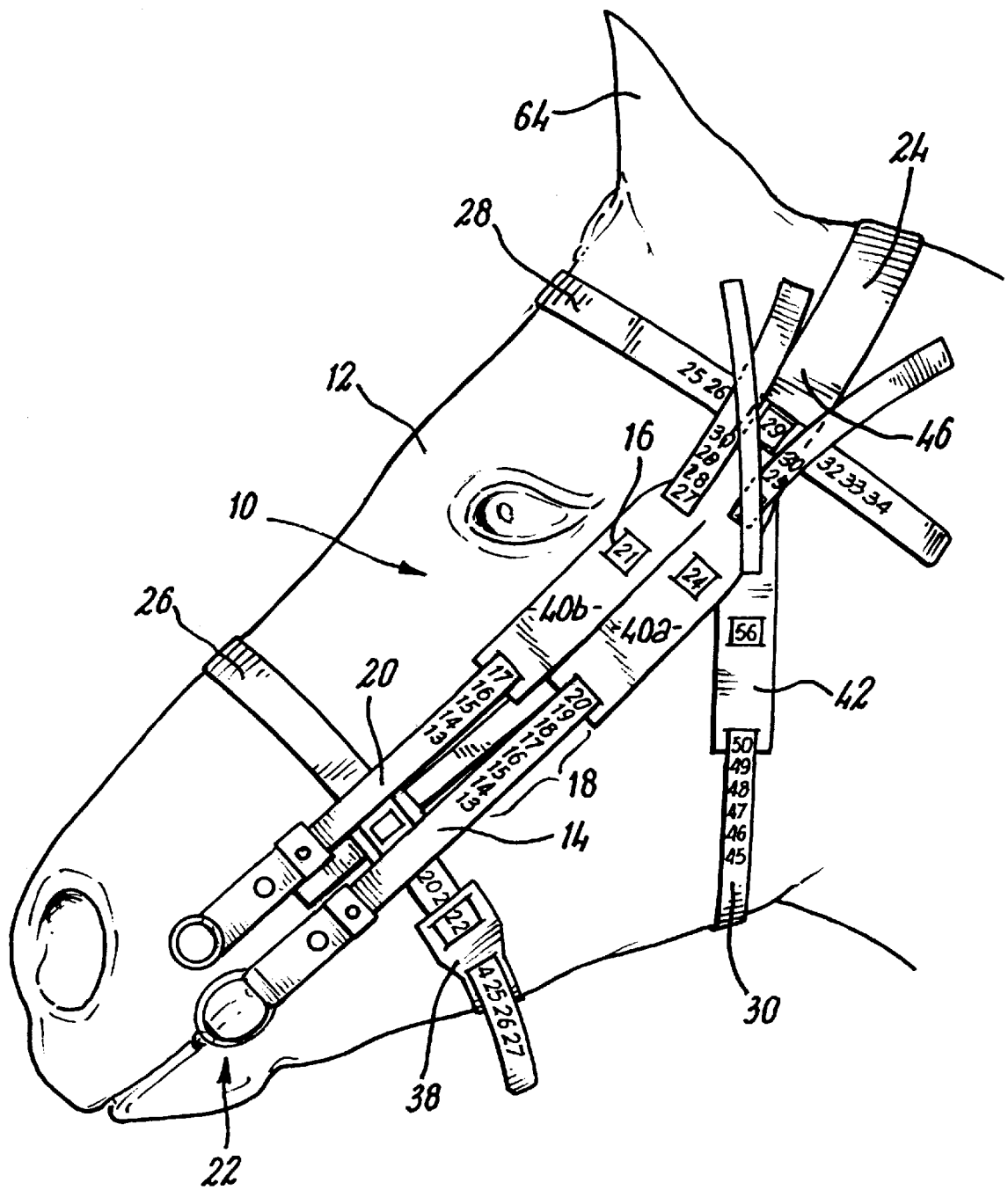
FIGS. 1 and 2 are schematic views of the near-side and off-side of a horse's head to which apparatus according to the present invention has been fitted.
Figure 2:
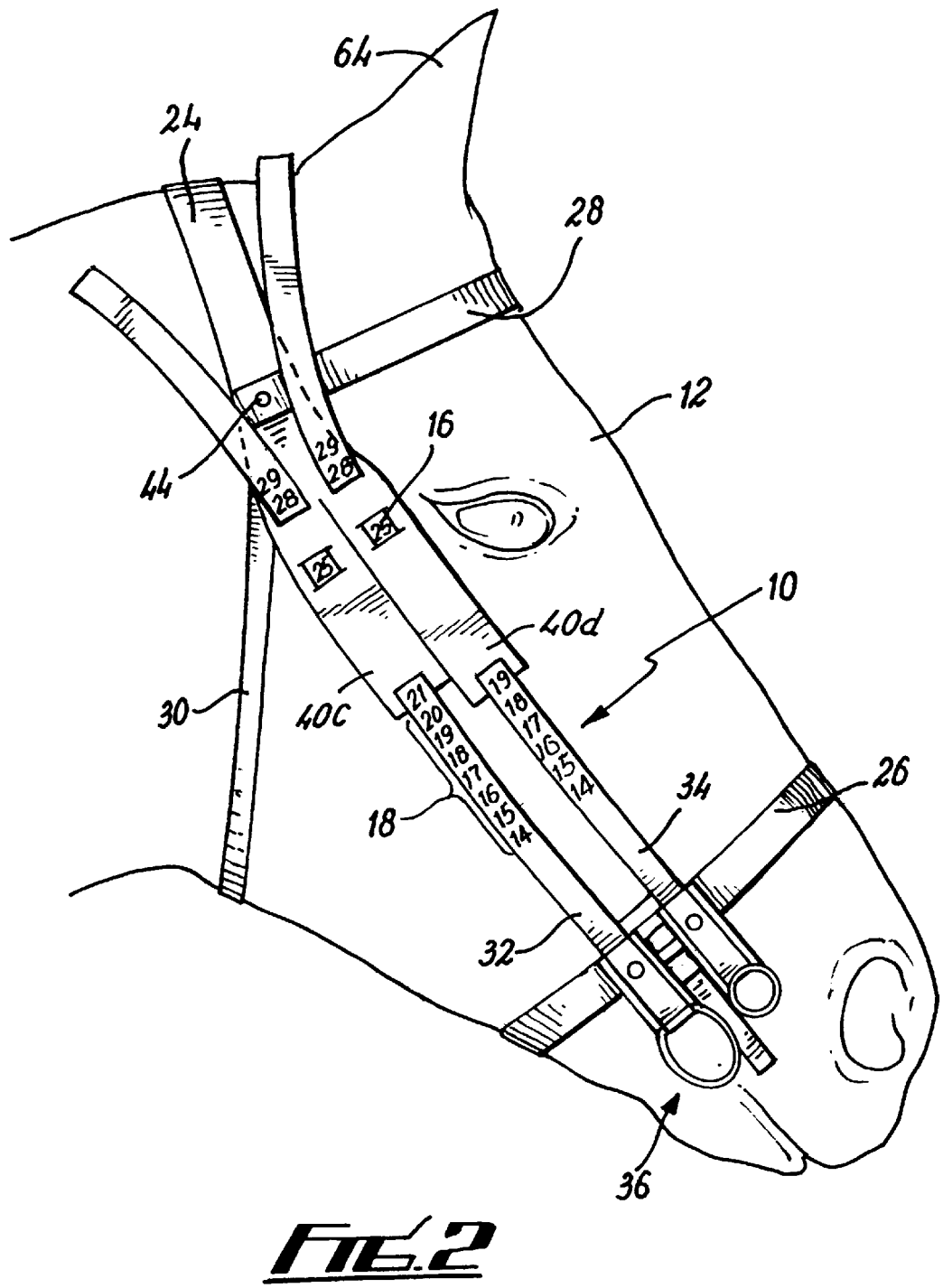

FIGS. 1 and 2 show horse head measuring apparatus 10 fitted to a horse head 12. The apparatus incorporates various pairs of components, such as cheek straps 14 each of which is movable (slidable) relative to another component to produce a desired fit of the apparatus 10 to the head 12. Measuring means in the form of a window 16 and numbers 18 provide a measurement of the relative positions of the slidable components.

Figure 4:
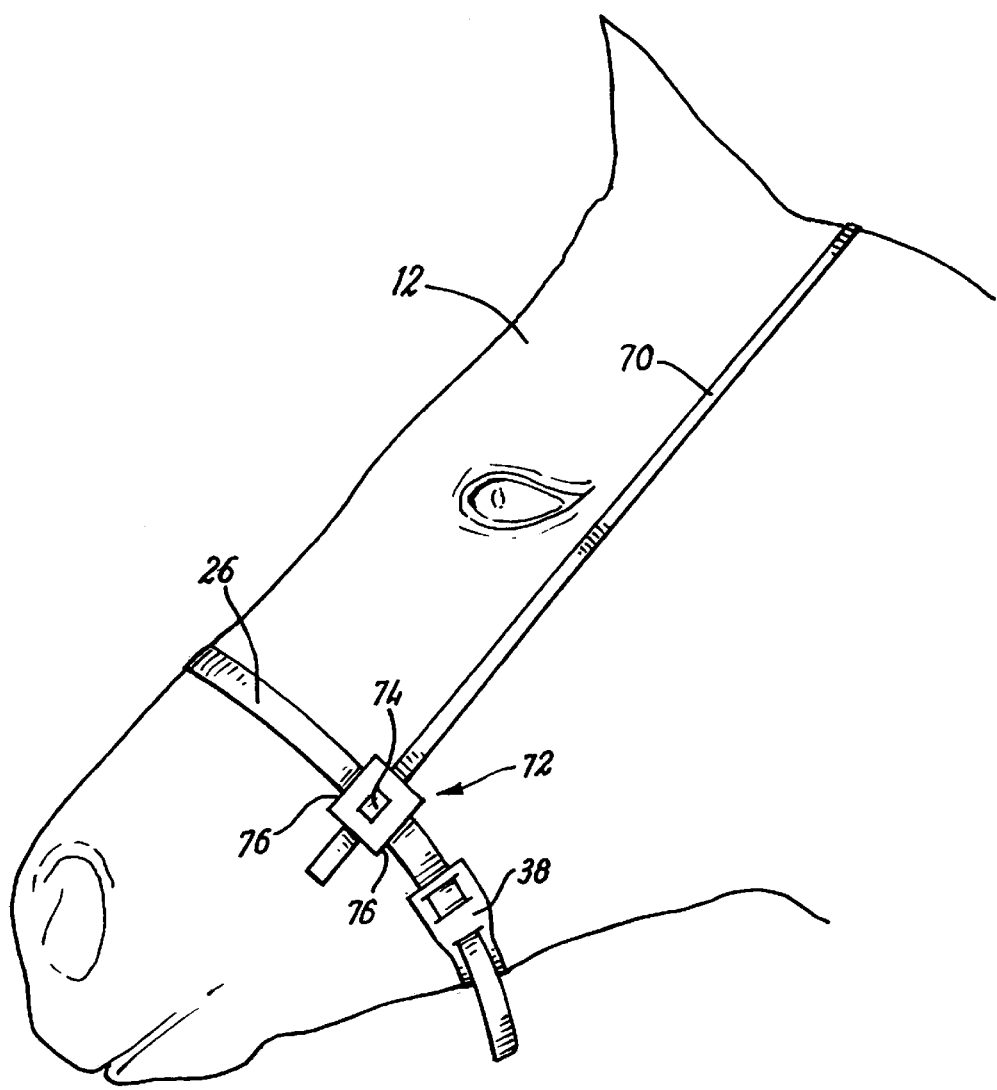
FIG. 4 is a schematic diagram showing a head strap with other components omitted for clarity.

In more detail, the apparatus 10 shown in FIGS. 1 and 2 forms a complete bridle for the horse's head, but could not be used for riding for reasons which will become apparent below. On the side shown in FIG. 1, two cheek straps 14,20 extend up from the bit at 22 to the head band 24. A nose band 26 and brow band 28 are provided over the front of the head. A throat lash 30 passes under the throat from the head band. On the other side (FIG. 2) another two cheek straps 32,34 extend from the other end of the bit at 36 to the head band 24. A head strap 70 extends over the head of the horse, but underneath the cheek straps and head band 24; the head strap is best seen in FIG. 4, from which all except the head strap 70, nose band 26 and the associated measuring device have been omitted for clarity.

Figure 3:
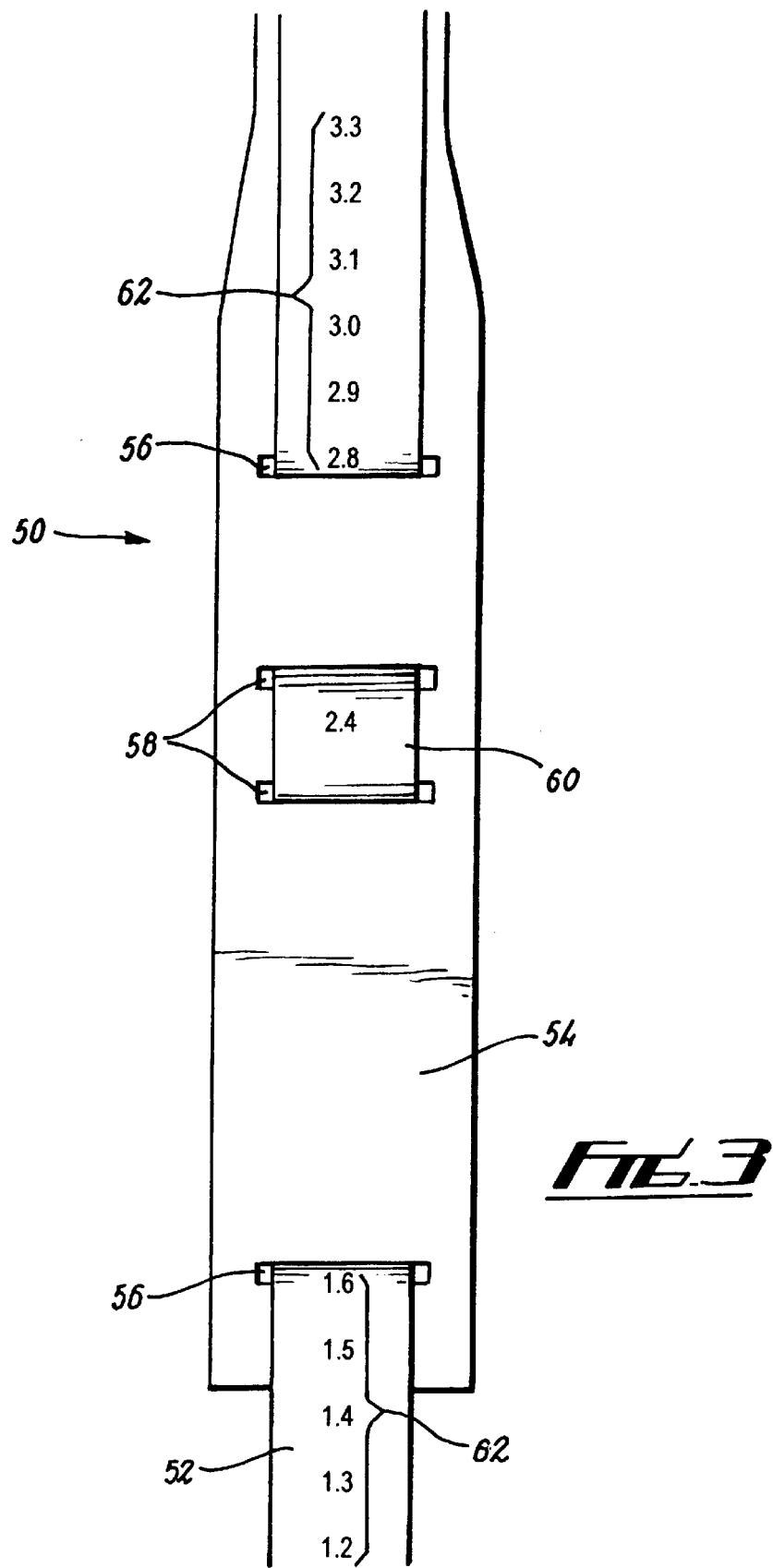
FIG. 3 shows a measuring device for use in the apparatus of FIGS. 1 and 2.

FIG. 3 shows an example of a measurement arrangement provided at various positions around the bridle 10, as follows. The nose band passes each way round the nose to join up again at a measurement device 38. The cheek straps 14,20,32,34 are each attached to the head band 24 by measurement devices 40a,b,c,d. The throat lash is permanently attached to the off-side of the head band (FIG. 2) and is connected on the near-side of the bridle (FIG. 1) to the head band by a measurement device 42. Similarly, the brow band is permanently attached at 44 to the off-side of the head band (FIG. 2) and is attached to the near-side of the head band (FIG. 1) by means of a measuring device 46.

Each of the measuring devices operates in the same manner and has the same form, apart from minor variations of size or shape arising from the location of the device in the bridle 10. Accordingly, it is convenient to describe one measurement device by reference to FIG. 3 and without relating the device to any particular device from FIGS. 1 and 2. Having understood the construction and operation of the device of FIG. 3, it is a simple matter, well within the powers of a person skilled in the art, to understand how each of the measurement devices of the bridle 10 will be constructed and will function.

Turning then to FIG. 3, the measurement device 50 has two components, namely a strap 52 and a window piece 54. The window piece 54 has four slits 56,58 formed perpendicular to the length of the strap 52. The two slits 58 are relatively close together. The strap 52 is threaded through the slits 56,58, so as to pass through the slits 58 in opposite directions and thus allow a short length 60 of the strap 52 to be visible between the slits 56, with the strap being obscured to either side of the slits 56 by material of the window piece 54. In effect, the slits 56 provide a window through which different parts of the strap 52 may be seen as the strap 52 slides relative to the window piece 54 through the slits 56,58.

Numerical markings or other indicia 62 are formed along the length of the strap 52. These indicia 62 correspond to measurements of components of a finished bridle. As the strap 52 is slid relative to the window piece 54 to lengthen or shorten the overall length of the two parts, different indicia 62 will become visible through the window. Accordingly, the strap and window piece can be adjusted until the bridle has achieved a desired fit on the horse's head, which will be comfortable, safe and aesthetically pleasing. Once that has been achieved, the number visible in the window of the window piece 54 can then be read and recorded to provide a measurement for constructing a functional bridle.

Returning now to FIGS. 1 and 2, it can be seen that when the apparatus 10 is first fitted to the head, the various measurement devices can be slid in either direction to lengthen or shorten various components of the apparatus 10, until a good fit is achieved. Adjustments can be made in any order, but it may be convenient first to adjust the brow band to ensure that the head band and brow band sit comfortably on the horse without pressing uncomfortably on the ears 64. The cheek straps 14,20,32,34 can then be lengthened or shortened at 40a,b,c,d to set the bit 22,36 at a height appropriate for the particular horse being measured. It may be desirable to provide releasable fittings at the bottom of the cheek straps, to allow fitting of the bit normally used with the horse being measured. This helps ensure that the particular bit will fit the particular horse correctly. The length of the nose band can then be adjusted at 38 to be a comfortable fit over the nose. Finally, the throat lash 30 can be adjusted at 42 until fitting correctly.

Figure 5:
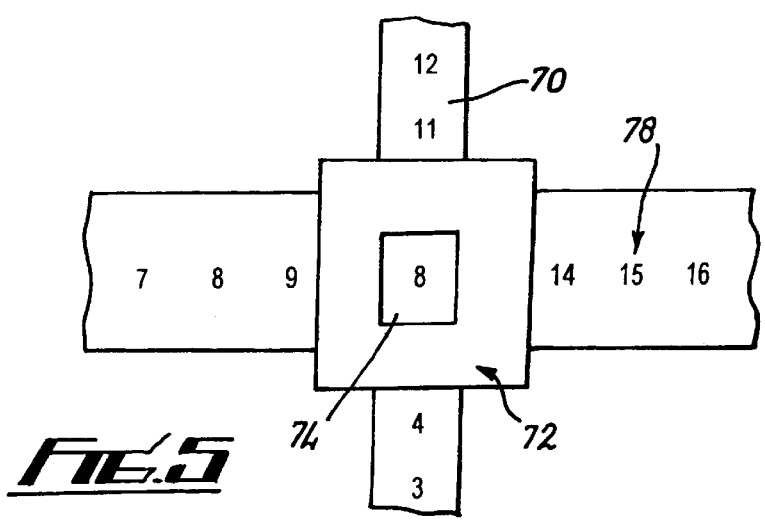
FIG. 5 shows a measuring device for use with the head strap of FIG. 4.

In addition to the measuring devices just described, the head strap 70 and nose band 26 are connected by the device 72 shown in FIG. 5. This has a window 74 through which the head strap 70 is visible and through which a measurement can be read in the manner described above. This measurement depends on the height of the nose band on the horse's nose, which will in turn be set for a variety of reasons of comfort and control. A device 72 is provided on both sides of the head, so that the required length of the head strap can be determined by taking a measurement from each of those devices. In addition to the length of the head strap, its stitching position along the nose band 26 can be determined by noting the position of the edges 76 of the device 72, with reference to the numbers 78 on the nose band 26. No windows are provided for this measurement but the edges of the device 72 provide a cursor for taking readings.

Adjustments at each of the measuring positions can be made and re-made until the user is satisfied that the apparatus 10 is correctly fitting the horse's head as required in a finished bridle. This judgement is partly aesthetic and partly judged by how tight or loose various parts of the straps are, where they sit in relation to the features of the head etc. Once the fit is approved, the measurements indicated by the windows of each of the measurement devices 38,40,42,46 can then be read and recorded to provide a complete set of measurements from which a bridle can then be manufactured. These measurements may be actual measurements of strap lengths required, or other indications from which strap lengths can be deduced.

Once a bridle has been constructed from those measurements, the manufacturer and user can be confident that the bridle will be a good, comfortable fit on the horse. In the finished article, buckles and straps would nevertheless be provided, partly to assist in putting the bridle onto the horse, and also to provide some further fine adjustment of the fit. It is convenient if the measurement devices are located at the position of these buckles in the final bridle, to further assist in achieving a good fit.

The result is a bridle which is made-to-measure for a particular horse. Indeed, it is possible to make a made-to-measure bridle even if the manufacturer cannot have direct access to the horse. For instance, a mail order arrangement could involve the manufacturer sending out an apparatus 10 to a prospective customer, who then fits it to their horse, reads off the measurements which result, and sends those back to the manufacturer, who can then make a made-to-measure bridle for that horse without having had direct access to the horse.

It may be desirable for the apparatus 10 to be made of leather in order to more closely resemble a real bridle and thus further assist the correct fitting. Alternatively, particularly in the mail order operation envisaged above, the apparatus could be made of very cheap, preferably disposable material such as linen tape, to be used once and discarded once the measurements had been sent back to the manufacturer. One advantage of using leather is that a relatively tight friction fit can be achieved in each of the measurement devices, thus helping the apparatus stay in the correct position while measurements are being taken. However, it will of course be realised that it would not be safe to use the apparatus 10 as a bridle while riding, because it would be not be secure or safe enough to withstand the forces encountered during riding.

Various modifications and variations can be made to the apparatus described above without departing from the scope of the present invention. In particular, the principles described, particularly the use of a measurement device as shown in FIG. 3, can readily be applied to alternative bridle styles, with the same results and advantages. Different materials could be used.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. Horse head measuring apparatus comprising two movable components that are movable relative to one another to produce a desired fit of the apparatus relative to the head, and measuring means operable to provide a measurement of the relative positions of said components, said measuring means comprising indicia on one of said components and indicator means on the other of said components, said indicator means serving, in use, to indicate one of said indicia as said measurement, and said indicator means comprising two apertures in said other component, said one component being threaded through both said apertures and in opposite senses, said one component being thereby visible between said apertures and obscured by said other component to either side of said apertures, and wherein the apparatus is in the form of a bridle.

2. The apparatus of claim 1, wherein said measurement is numerical.

3. The apparatus of claim 1, wherein said measurement represents the length required of a strap of a finished harness article having the desired fit to the head being measured.

4. The apparatus of claim 3, wherein said finished harness article is a bridle.

5. The apparatus of claim 1, wherein said measuring means is provided at each position at which an adjustable connection will be provided for a strap in a bridle to be made from the measurements, whereby a required length of each strap in said bridle is represented by respective indicia after said apparatus has been adjusted to provide a desired fit to a head.

6. A method of measuring a horses's head, comprising:

providing measuring apparatus in the form of a bridle and including two movable components that are movable relative to one another to produce a desired fit of the apparatus relative to the head, and measuring means operable to provide a measurement of the relative positions of said components, said measuring means comprising indicia on one of said components and indicator means on the other of said components, said indicator means serving, in use, to indicate one of said indicia as said measurement, and said indicator means comprising two apertures in said other component, said one component being threaded through both said apertures and in opposite senses, said one component being thereby visible between said apertures and obscured by said other component to either side of said apertures, offering the apparatus to said head, adjusting said components relative to one other to achieve a desired fit to said head, and using the measuring means to provide a measure of the relative positions of the components.

7. The method of claim 6, comprising moving said relatively movable components until a desired overall fit is achieved by said apparatus, and reading measurements from said measurement means.

8. The method of claim 7, wherein a manufacturer dispatches said measuring apparatus to a prospective customer, said customer fits said apparatus to a head, records measurements provided by said measurement means, and provides said recorded measurements to said manufacturer, whereby said manufacturer is enabled to produce a made-to-measure harness article without access to said horse.

* * * * *